United States Patent [19]

Noetzel et al.

[11] Patent Number: 4,568,706
[45] Date of Patent: Feb. 4, 1986

[54] MACROPOROUS BEAD POLYMERS, A PROCESS FOR THEIR PREPARATION AND THEIR USE

[75] Inventors: Siegfried Noetzel, Kelkheim; Otto Mauz, Liederbach; Klaus Sauber, Bad Soden am Taunus, all of Fed. Rep. of Germany

[73] Assignee: Hoechst Aktiengesellschaft, Fed. Rep. of Germany

[21] Appl. No.: 614,137

[22] Filed: May 25, 1984

[30] Foreign Application Priority Data

May 28, 1983 [DE] Fed. Rep. of Germany ....... 3319506
Feb. 6, 1984 [DE] Fed. Rep. of Germany ....... 3404021

[51] Int. Cl.$^4$ .............................................. C08J 9/00
[52] U.S. Cl. ..................................... 521/149; 521/56; 526/304; 526/307
[58] Field of Search .................. 521/56, 149; 526/304, 526/307

[56] References Cited

U.S. PATENT DOCUMENTS 3,594,333  7/1971  Buss et al. ............................ 521/149
4,154,910  5/1979  Tanaka et al. ....................... 521/149
4,246,362  1/1981  Sasaki et al. ........................ 521/149
4,256,843  3/1981  Sasaki et al. ........................ 521/149

Primary Examiner—Morton Foelak
Attorney, Agent, or Firm—Finnegan, Henderson, Farabow, Garrett & Dunner

[57] ABSTRACT

The invention relates to bead polymers based on monomers of the formula

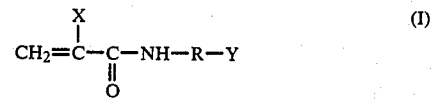

in which X is hydrogen or methyl, R denotes an aliphatic hydrocarbon radical having 1 to 12 carbon atoms, and Y denotes OH or $NH_2$, which have been prepared using a special dispersion stabilizer. They are particularly distinguished by high porosity and are very suitable as carrier materials for biologically active substances.

16 Claims, No Drawings

MACROPOROUS BEAD POLYMERS, A PROCESS FOR THEIR PREPARATION AND THEIR USE

The binding, via covalent bonds, of biologically active substances, such as enzymes, antibodies, antigens, hormones and the like, with retention of their activity, to polymeric carrier materials, in order by this means, for example, to stabilize or purify enzymes or make them insoluble in water, is known. Biologically active substances immobilized in this manner offer considerable advantages compared with the soluble form: on the one hand, the removability, by sedimentation, after completion of a reaction is simplified and, on the other hand, the stability and reusability of the products are multiplied.

Swellable, crosslinked bead polymers, which are obtained by copolymerization of monomers containing reactive groups, crosslinked monomers and hydrophilic monomers, are described as carrier substances in German Auslegeschrift 2,237,316. The reactive groups disclosed in this are the halogenoalkyl, the epoxide, the carbonyl chloride, carboxylic anhydride, carbonyl azide, carboxylic phenyl ester and hydroxamic acid groups. However, these carrier materials have a number of disadvantages; thus the immobilization of biologically active substances on some of them is a rather lengthy process, the activity of some of them is unsatisfactory and moreover, when using the anhydride variants, charges are introduced.

The introduction into a hydrophilic polymer of oxirane groups which can then be used for bonding a biologically active substance is known from German Offenlegungsschrift 2,102,514. The hydrophilic polymers mentioned include those containing acrylamide groups. However, these carriers lack the morphology of the bead form and the porous structure. Thus, for example, they cannot be used for column processes.

The object of the present invention was to provide a polymeric material, in particular as a carrier material for biologically active substances, based on (meth)acrylamide derivatives, which does not have the disadvantages of the state of the art and which, in particular, is in the form of beads and has adequate porosity. Another object was to develop a process suitable for this purpose.

To achieve this object, the invention proposes a polymer which is essentially composed of units which are derived from monomers of the formula

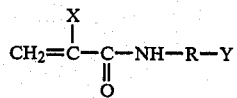

in which X is hydrogen or methyl, R denotes an aliphatic hydrocarbon radical having 1 to 12 carbon atoms, and Y represents OH or $NH_2$, and of units which are derived from at least one other monomer which can be copolymerized with monomers of the formula (I), the mean particle size of the polymer particles being in the range from 20 to 800 μm, which comprises the polymer particles having an essentially spherical shape and a mean pore diameter of 5 to 2,000 nm.

In addition, the invention relates to a process for the preparation of polymers of this type of polymerization of compounds of the formula

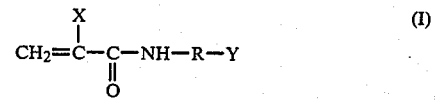

in which X, R and Y have the abovementioned meaning, with at least one other monomer which can be copolymerized with it, the polymerization being carried out in a liquid dispersing agent which, under the polymerization conditions, does not dissolve the monomers and the polymer, in the presence of a radical initiator and a dispersion stabilizer, which comprises using, as the dispersion stabilizer, a copolymer of maleic anhydride and a vinyl alkyl ether having 6 to 30 carbon atoms in the alkyl group, or a vinyl ester having 6 to 30 carbon atoms in the carboxylic acid group, or a relatively long-chain α-olefin having 8 to 30 carbon atoms.

The invention also relates to the use of the polymers thus obtained, preferably after reaction with spacers, as carrier materials for the preparation of carrier-bound biologically active substances.

The polymer according to the invention advantageously contains the units which are derived from the monomers of the formula (I) in amounts of 5 to 90 mole-%, preferably 10 to 80 mole-%, and in particular 15 to 60 mole-%, relative to the total polymer. In principle, amounts which are larger or smaller than those indicated above are possible but, as a rule, this is associated with disadvantages. The optimal amount within the ranges indicated above depends, inter alia, on the desired site density, on the molecular weight of the biologically active substance and the like.

As already mentioned, the radical R in the abovementioned formula (I) has the meaning of an aliphatic hydrocarbon radical having 1 to 12 carbon atoms, which can be linear, branched or cyclic (cycloaliphatic). The radical R is preferably an alkylene radical having 1 to 6 carbon atoms. Examples of this which may be mentioned are: methylene, ethylene, propylene, isopropylene, n-butylene, i-butylene, pentylene, hexylene, 2-ethylhexylene, cyclopentylene, cyclohexylene, methylenecyclohexyl and the like. The radical Y in the abovementioned formula (I) preferably represents the OH group, and this in turn is preferably primary. Accordingly, appropriate monomers of formula (I) are N-methylol(meth)acrylamide, N-(2-hydroxyethyl)-(meth)acrylamide, N-(3-hydroxypropy)(meth)acrylamide, N-(2-hydroxypropyl)(meth)acrylamide, N-(2-aminoethyl)(meth)acrylamide, N-(3-aminopropyl)-(meth)acrylamide, N-(6-amino-hexyl)(meth)acrylamide etc. It is also possible to use mixtures of monomers of these types.

Part at least, preferably at least 0.5 mole-%, and in particular 1 to 40 mole-%, of the radical Y in the polymer according to the invention is reacted with so-called spacers. In general, the amount of spacer will not exceed about 0.1 mole-% to 20 mole-%, preferably 1 to 10 mole-%, relative to the total of monomer units, in the bead polymer according to the invention.

Spacers are to be understood to be compounds which both react with the radical Y of the (—CONH—R—Y) side chain of the bead polymer according to the invention and introduce a reactive group, preferably an epoxy group, which can then react with the biologically active substance. Thus, part at least of the radical Y is, after the reaction with the spacer, replaced by the group

Y'—B—Z     (II)

in which Y' is O or NH, B represents an organic radical (the spacer in the stricter sense), in particular a hydrocarbon radical having 1 to 12 carbon atoms, which can optionally be interrupted by heteroatoms, such as O, NH, S etc., and Z represents a functional group which can undergo covalent bonding with the biologically active compound. This includes, for example, the groups

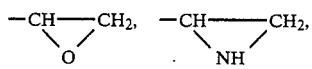

COX (X=H, halogen, —N₃, —OR; R=alkyl radical having 1 to 6 carbon atoms), —CH(OR)₂ (R as above),

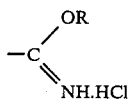

(R as above), —N₂]⁺ or —NCO.

Y' preferably denotes oxygen, B an aliphatic, in particular unbranched, hydrocarbon radical having 1 to 6 carbon atoms, an aryl radical or an alkylaryl radical, and Z denotes

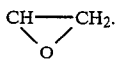

The following are examples of the Y'—B—Z group:

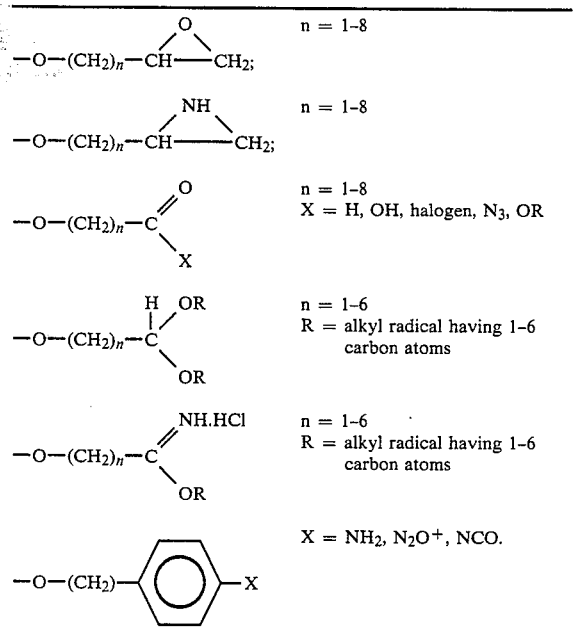

According to the invention, the bead polymer also contains at least one additional monomer unit which is derived from a monomer which can be copolymerized with the monomer of the formula (I). Preferably, this takes the form of two other monomer units which differ from one another.

One of these monomer units is preferably derived from a monomer having hydrophilic groups, and this provides the polymer employed as carrier with adequate hydrophilicity and adequate swellability in water. This is of importance inasmuch as the bonding reaction with the biologically active substance is usually carried out in an aqueous system, and the hydrophilic biologically active substance must be able to diffuse up to the carrier material. These monomers include, for example, the monomers listed as component (c) in German Offenlegungsschrift 2,237,316. Those which are preferred within the scope of the present invention are: N-vinylpyrrolidone, (meth)acrylamide, alkyl(meth)acrylates each having 2 to 6 carbon atoms in the alkyl group, hydroxyalkyl(meth)acrylates having 2 to 6 carbon atoms in the alkyl group, N-vinyl-N-alkylacetamide(C₁-C₄-alkyl), vinyl acetate or vinylene carbonate. The latter two monomers in fact do not provide the polymer with hydrophilic properties until appropriate hydrolysis has been carried out. Where appropriate, it is also possible for several of these hydrophilic monomer units to be present.

The ratio of the monomer of formula (I) to the hydrophilic component in the polymer also depends on the type of enzyme to be bonded. When the molecular weight of the enzyme, or of the substrate with which the enzyme is intended to react, is very high, it is advantageous to increase the molar ratio in favor of the hydrophilic component, since neighboring spacer groups which are capable of bonding do not succeed in reacting, for steric reasons, and may possibly even interfere. Furthermore, the amount of hydrophilic component is also governed by the amount of the crosslinking component which is preferably present according to the invention. As a rule, the greater the amount of the latter, the greater also the amount of hydrophilic component which will be necessary to provide the carrier polymer with sufficient hydrophilicity and swellability. In general, the amount of hydrophilic monomer unit(s) in the polymer according to the invention is 5 to 70 mole-%, preferably 20 to 50 mole-%, and in particular 30 to 50 mole-%, relative to the polymer. In any event, the hydrophilicity of the polymer is adequate in the case where the polymer is soluble in water without also using a crosslinker (see below). As a rule, the swellability in water is adequate when the polymer, after crosslinking, swells to up to 30 times, preferably to 3 to 10 times, its original bulk volume.

The polymer according to the invention preferably contains, as the other compound which can be copolymerized with the monomer of formula (I), crosslinking monomer units as are known from the state of the art. Typical representatives which may be mentioned here are: divinyl ethers of glycols, such as ethylene glycol divinyl ether, butanediol divinyl ether, hexanediol divinyl ether, N,N'-alkylenebis(meth)acrylamides having straight-chain or branched alkylene radicals containing up to 12 carbon atoms, preferably up to 6 carbon atoms, such as N,N'-methylenebisacrylamide, N,N'-ethylenebisacrylamide, N,N'-hexamethylenebisacrylamide, N,N'-methylenebismethacrylamide, N,N'-ethylenebismethacrylamide, N,N'-hexamethylenebismethacrylamide, N,N'-ethylidenebisacrylamide, glyoxalbisacrylamide, 1,2-bisacrylamido-1,2-dihydroxyethane, bisacrylamidoacetic acid, ethylene glycol dimethacrylate, butanediol dimethacrylate, triallyl cyanurate, trisacryloyl perhydrotriazine, divinylbenzene, divinyl adipate, N,N'-divinylethyleneurea, N,N'-divinylpropyleneurea, ethylidenebis-3-(N-vinylpyrrolidone),N,N'-divinyl-2,2'-diimidazolyl and 1,1'-bis(3,3'-vinylbenzimidazolin-2-one)-1,4-butane, vinyl acrylate, allyl methacrylate, inter alia. It is also possible for several different crosslinking monomer units to be present. Some of these crosslinkers, for example N,N'-divinylethyleneurea, N,N'-divinylpropyleneurea, ethylidenebis-3-(N-vinylpyrrolidone), N,N'-divinyl-2,2'-diimidazolyl and 1,1'-bis(3,3'-vinylbenzimidazolin-2-one)-1,4-butane, or N,N'-methylenebisacrylamide can also contribute to the hydrophilicity of the polymer.

The amount of the crosslinking monomer unit, and thus the density of crosslinking, in the polymer depends on its use. A low density of crosslinking can be advantageous for enzyme reactions in stirred vessels or for diagnostic aids; on the other hand, if used for column packing, high stability of shape of the bead polymer, and thus high density of crosslinking, is a prerequisite. Thus, depending on the type of use, the amount of crosslinking monomer unit can be up to 60 mole-% relative to the polymer. It is preferably between 1 and 50 mole-%, and in particular between 5 and 40 mole-%. As already stated above in this context, the amount of crosslinking component has a certain relationship with that of the hydrophilic component. The amount of crosslinking monomer will usually be selected such that the bead polymer swells in tetrahydrofuran by up to 14 times, preferably 0 to 8 times, its original bulk volume.

Water-soluble carriers are of interest when the reaction of the carrier with the biologically active substance is to be carried out in an aqueous solution of the carrier.

Where appropriate, a non-crosslinked carrier polymer can also be crosslinked in a known manner by subsequent chemical reaction, for example with diisocyanates. In this case, the polymer should contain a somewhat higher proportion of units derived from monomers of formula (I).

Other non-hydrophilic and non-crosslinking monomer units which can optionally be pressent are, for example, those which are derived from: acrylic and methacrylic esters having 5–12 carbon atoms in the alkyl radical, (meth)acrylonitrile, vinyl esters having 4–18 carbon atoms in the carboxylic acid radical, such as vinyl butyrate and vinyl stearate, and vinyl esters of branched carboxylic acids having 10 to 12 carbon atoms; also vinylaromatics, such as styrene or α-methylstyrene. These monomer units can be present in the polymer in amounts of 4 to 40 mole-%, preferably 8 to 20 mole-%, relative to the polymer.

The bead polymer according to the invention is predominantly composed of spherical particles, the mean particle size of which in the dry, non-swollen state is 20 to 800 μm, preferably 50 to 300 μm, the particle size distribution preferably being narrow. The particular optimum particle size of the polymer depends, in particular, on the specific area of use. For example, in a column process carried out under atmospheric pressure, it will be possible to select the particle size, within the limits mentioned above, to be correspondingly larger than for a process under elevated pressure. The beads of the bead polymer according to the invention are principally formed as macroporous beads. This is evident by the mean pore diameter which results according to the invention being in the range from 5 to 2,000 nm, preferably 10 to 1,000 nm.

The determination of the pore diameter (pore volume) is carried out in such a manner that first the pore volume is determined by the capillary pressure method (mercury porosimetry) (cf. in this context "Ullmanns Encylopädie der technischen Chemie" [Ullmann's Encyclopedia of Industrial Chemistry] volume 5, (1980), pages 751–752). The mean pore diameter then results from this by calculation using the equation given in this literature citation on page 752, top of the left-hand column. In addition, a determination of the pore size is also possible by scanning electron microscopy.

The bead polymers according to the invention are particularly suitable as carriers for biologically active substances. However, they can also be employed for other purposes, for example as ion exchangers, adsorbents for chromatographic processes and the like.

The process according to the invention for preparing these bead polymers is carried out under the customary and known conditions for bead polymerization, as are described, for example, in German Offenlegungsschrift 2,237,316 or German Offenlegungsschrift 2,556,759, but with the innovation that special dispersion stabilizers are used.

These are preferably alternating copolymers of maleic anhydride and a vinyl alkyl ether, preferably a vinyl n-alkyl ether having 6 to 30 carbon atoms, preferably 10 to 20 carbon atoms, in the alkyl group, or a vinyl ester having 6 to 30 carbon atoms, preferably 10 to 20 carbon atoms, in the carboxylic acid group, or a relatively long-chain α-olefin having 8 to 30 carbon atoms, preferably 10 to 20 carbon atoms. Examples of these types of vinyl alkyl ethers, vinyl esters and relatively long-chain α-olefins which may be mentioned here are: vinyl octyl ether, vinyl decyl ether, vinyl dodecyl ether, vinyl stearyl ether, vinyl myricyl ether, vinyl ethylhexanoate, vinyl isononanoate, vinyl versatate, vinyl laurate, vinyl stearate, and vinyl esters of branched carboxylic acids having 10 to 12 carbon atoms; 1-octene, 1-decene, 1-dodecene, 1-tetradecene, 1-octadecene and 1-tricosene.

These dispersion stabilizers are effective in amounts as little as 0.001% by weight relative to the total amount of monomers. Usually, amounts of 0.005 to 10% by weight, preferably 0.01–5% by weight, (relative to the total amount of monomers) are used.

The reduced specific viscosity (RVS) of these copolymers which are employed as dispersion stabilizers is, as a rule, between 0.01 and 1.0 dl/g (determined in 0.6% strength solution in toluene at 25° C). The corresponding range which is preferred for the copolymers of maleic anhydride and vinyl alkyl ethers or vinyl esters is 0.05 to 1.0 dl/g, and for the copolymers of maleic anhydride and relatively long-chain α-olefin is 0.01 to 0.1 dl/g. The molar ratio between maleic anhydride and the vinyl alkyl ether or vinyl ester or the relatively long-chain α-olefin is generally between 1:4 and 1:1, preferably between 1:2 and 1:1, and in particular 1:1.

Those radical initiators which are suitable according to the invention are those which are readily soluble in the monomer phase and have as a low a solubility as possible in the liquid dispersing agent. Examples of these are organic peroxides, such as di-tert.-butyl peroxide, dibenzoyl peroxide, bis(o-methylbenzoyl)-peroxide, tert.-butyl hydroperoxide, cumene hydroperoxide, diisopropyl peroxydicarbonate, cyclohexanone peroxide or aliphatic azo compounds, such as α,α'-azodiisobutyronitrile, azobiscyanovaleric acid, 1,1'-azocyclohexane-1,1'-dicarbonitrile and azodicarbonamide. When using water or mixtures of water with water-soluble substances as the inert agent, water-soluble initiators, such as ammonium, sodium and potassium peroxydisulfate, cyclohexyl carbonatopotassium sulfatoperoxide, succinoyl peroxide and tert.-butyl permaleate, are employed. Appropriate redox systems may also optionally be used. The amount of initiator is usually 0.01 to 5, preferably 0.1 to 2, % by weight (relative to the total amount of monomers).

The liquid dispersing agents used for carrying out the bead polymerization according to the invention are, in particular, those organic compounds which are liquid under normal conditions, have a boiling point above 60° C., preferably in the range 85°-300° C., and which either do not dissolve or, in any event, only dissolve traces of the monomers, the polymer and, preferably, also the initiator under the polymerization conditions, in order to suppress undesired emulsion polymerization. Hydrocarbons having 6 to 20, preferably 12 to 16, carbon atoms in particular paraffins, for example, are well suited. It is also possible to use a mixture of various compounds as the dispersing agent. Examples of suitable hydrocarbons or mixtures of hydrocarbons are n-hexane, n-heptane, n-octane, cyclohexane, isooctane, petroleum fractions with boiling ranges between 90° and 170° C., and low viscosity liquid paraffin (Deutsches Arzneibuch [German Pharmacopeia], 7th edition, DAB 7). The ratio of the monomer phase to the dispersing agent phase can vary within wide limits, for example between 1:1 to 1:50, preferably 0:5:1 to 1:15 (ratio by weight).

In order to achieve as high a porosity of the bead polymer as is possible, preferably certain inert, liquid components (inert agents) are added to the polymerization system or, preferably, to the monomers. These components are to be understood to be those materials in which the monomers are readily soluble or with which the monomers are miscible, but which, on the other hand, are virtually insoluble in the dispersing agent and thus are not miscible with it. According to their behavior toward the appropriate copolymers, the inert agents can be divided into swelling and/or precipitating agents. In the case of a hydrophilic matrix, polar inert agents will, as a rule, favor swelling, such as, for example, dimethylformamide, dimethyl sulfoxide, dioxane, water, etc., while non-polar substances, such as glycerol triacetate etc., prove to be precipitating agents for the copolymer. The optimal inert agent or mixture of inert agents can readily be determined by a few simple routine experiments. In particular, when bead polymers having relatively low degrees of crosslinking are aimed at, it may well be advisable to use a mixture of a polar and a non-polar inert agent. The inert agents do not participate in the polymerization, but are coated by the polymer and are dissolved out again during work-up. This produces permanent pores. The pore size can be affected by the type and amount of the inert agent, but also depends on the amount of crosslinking component.

The inert agents can be used alone or in mixtures. Examples which may be mentioned are: methanol and its higher homologs, ethylene glycol, methylglycol, propylglycol, diethylene glycol, triethylene glycol, 1,4-butanediol, glycerol, polyethylene glycols, polypyrrolidones, diethylene glycol dimethyl ether, glycerol triacetate, ethylene carbonate, formamide, dimethylformamide, dimethyl sulfoxide, dioxane, water etc.

The amount of inert agent added can be widely varied. It depends, inter alia, on the monomer composition of the carrier, in particular its content of crosslinker, the desired porosity (pore size) and on the exact intended use of the carrier polymer. Thus, when the degree of crosslinking is high, a correspondingly large amount of inert agent is advisable in order to achieve a specified porosity (pore size). Equally, at one and the same degree of crosslinking, the porosity (pore size) will be larger the more inert agent is employed. Obviously, this can only be increased within certain limits, since otherwise the thickness of the walls of the macroporous beads, and thus their mechanical stability, becomes too low. In most cases, an amount of inert agent which corresponds to 0.02 to 5 times, preferably 0.04 to 3 times, the amount of monomers employed will provide satisfactory results.

The amounts of the monomer of formula (I) and of the other comonomer(s) used are such that the resulting polymer has the previously mentioned amounts of monomer units. With this aim, the monomer of formula (I) is used, as a rule, in amounts of 5 to 90 mole-%, preferably 10 to 80 mole-%, relative to the total mixture of monomers. On the other hand, the amount of hydrophilic monomer is usually 5 to 70 mole-%, preferably 20 to 50 mole-%, relative to the total mixture of monomers, and the amount of crosslinking monomer, when employed, is up to 60 mole-%, preferably 1 to 50 mole-%, relative to the total amount of monomers.

The monomers of formula (I) are prepared in a known manner, for example by reacting (meth)acryloyl chloride with compounds of the formula $H_{2N-R-Y}$ in the presence of suitable acid acceptors.

The process according to the invention is advantageously carried out in a reaction vessel which is provided with a stirring device, at temperatures of, usually, 20°-150° C., preferably 65°-125° C. The particle size of the bead polymer is adjusted in a known manner by the speed of stirring and the phase ratio. It is particularly advantageous to use a vertical cylindrical vessel with a flat base, which is provided with a stirrer which is located coaxially and the shaft of which almost reaches the base of the vessel. The reaction vessel is preferably vacuum-tight and can be provided with a reflux condenser, addition funnel, gas-introduction tube and temperature-measuring device. The heating and cooling of the vessel is generally brought about by a liquid bath, for example an oil bath or water bath.

It is advantageous to carry out the process according to the invention with the exclusion of atmospheric oxygen. Thus, the reaction vessel is flushed before starting with an inert gas, preferably nitrogen.

After completion of the polymerization reaction, the unreacted monomers are removed from the reaction vessel, for example by evaporation under reduced pressure, preferably under a pressure of 0.1-15 Torr. After removing the residual monomers, the dispersing agent is separated from the solid polymer, for example by decantation, filtration or aspiration of the supernatant. The polymer is then, where necessary, washed with a low-boiling organic solvent, for example a hydrocarbon, a lower alcohol or acetone, and finally dried. The polymer is usually dried at a temperature of 20° to 100° C., preferably 40° to 80° C.; drying under reduced pressure is advisable.

When the bead polymer according to the invention is used as a carrier material for biologically active substances, it is, as already mentioned, preferably initially reacted with spacers. Suitable spacers according to the invention are the known homo- and hetero-bifunctional compounds whose second functional group undertakes the coupling with the biologically active substance to be bound (cf. German Pat. Nos. 2,421,789 and 2,552,510, and Ullmanns Encyclopädie der technischen Chemie, 4th edition, Vol. 10, page 540 and "Characterization of Immobilized Biocatalysts", Verlag Chemie, Weinhem, 1979, page 53). According to the invention, those compounds which are preferably used as spacers are those which introduce epoxide groups, such as epichlorohydrin or its homologs ($\alpha,\beta'$-epoxy-$\omega$-halogenoalkanes) and diepoxides, such as ethylene glycol 1,2-diglycidyl ether and 1,4-butanediol diglycidyl ether.

The reaction with, for example, the spacers containing epoxide groups, is carried out in a manner known per se using excess amounts of epoxide compounds at temperatures of 50° to 200° C., generally for two to six hours, preferably in the presence of basic catalysts, such as tertiary amines, alkalis, dimethylformamide etc., and optionally using inert diluents, such as dioxane etc. The epoxidized polymer particles are isolated likewise in a known manner by filtration with suction and thoroughly washing with low-boiling organic solvents which do not attack the polymer particles, such as acetone or diethyl ether. The inert organic washing agents are then removed at 40° to 60° C. and under reduced pressure (200 mm Hg), passing over nitrogen, in a vacuum drying oven.

It emerges, surprisingly, that the polymers containing epoxide groups which are thus obtained have a considerably higher activity than the products obtained according to German Auslegeschrift 2,237,316 by direct polymerization of monomers containing epoxide groups.

The term "biologically active substances" is to be understood to be the known natural or synthetically prepared substances which are active in vivo or in vitro, such as enzymes, activators, inhibitors, antigens, antibodies, vitamins, hormones, effectors, antibiotics, proteins and the like. In this context, the latter term also includes proteins having certain non-protein substituents, such as metal ions, polysaccharides, porphyrin groups, adenine dinucleotide, ribonucleic acid, phospholipids etc. Polypeptide fragments, for example the active moieties of enzyme molecules, are also comprised by the term biologically active substances.

Of the biologically active substances mentioned above, the enzymes are preferred according to the invention. Examples of enzymes are adenyl deaminase, alcohol dehydrogenase, asparaginase, carboxypeptidase, chymotrypsin, diphosphoesterase, $\alpha$-glucosidase, glucose isomerase, glucose oxidase, glucose-6-phosphate dehydrogenase, hexokinase, invertase, $\beta$-lactamase, lactase, lactic dehydrogenase, various lectins, NAD kinase, neuraminidase, papain, peroxidase, phosphatases (alkaline and acid), 5'-phosphodiesterase, pyruvate kinase, ribonuclease and trypsin.

Examples of other biologically active substances are hormones, such as insulin and the wide variety of pituitary hormones, proteins of the gamma-globulin fraction, for example antibodies of classes G, M, A, D and E, other blood factors, for example antihemophilic factor, the coagulation factors, specific antibodies, for example hepatitis, poliomyelitis, measles, mumps, influenza or rabbit antibodies, antigens, such as hepatitis, poliomyelitis, measles, mumps, influenza or rabbit antigens for purification or stimulating suitable antibody reactions, the antigen (after being made insoluble) remaining in the insoluble form and consequently being unable to penetrate into the body and harm it, as well as general body proteins, such as hemoglobin or albumin.

The bonding reaction of the biologically active substance is carried out in a known manner, such as is described, for example, in German Offenlegungs-schrift 2,407,340 or in German Pat. Nos. 2,215,687, 2,421,789 and 2,552,510. The reaction is usually carried out at room temperature or at a temperature below this. The latter applies, in particular, when the biologically active substance to be bonded is inherently unstable; in this case, the temperatures are then below $+10°$ C., preferably at 0° to $+5°$ C.

The bonding reaction is preferably carried out at a pH in the neighborhood of neutrality, for example at pH 5 to 9, since most biologically active substances are most stable in this range. Nor is it necessary, as a rule, to maintain strongly acid or alkaline conditions, since the macroporous bead polymers according to the invention react rapidly even in the neutral range with most of the substances in question. The bond which is produced thereby provides sufficient stability for long storage and high stability on use.

Preferably about 10 to 80 parts by weight of the carrier polymer, in particular one which contains at least 50 mole-% of units of monomers of the formula (I), are used per 1 part by weight of the biologically active substance to be bonded. It is advantageous to employ larger amounts of the carrier polymer in those cases where the units of monomers of the formula (I) amount to less than 50 mole-% of the polymer.

The invention is illustrated in detail by the examples which follow.

PREPARATION OF A DISPERSION STABILIZER (copolymer of maleic anhydride and vinyl stearyl ether)

98 g of maleic anhydride (1 mole) and 296 g of vinyl stearyl ether (1 mole) in 250 ml of acetone were initially introduced into a stirred flask, 5 ml of diisopropyl percarbonate (40% strength solution in phthalate) were added, and the mixture was polymerized, with stirring under nitrogen, at 60° C. for 5 hours.

After cooling, the precipitated product was filtered off with suction and washed several times with acetone. The molar ratio of the two monomers in the copolymer was 1:1; the RSV value was 0.224 dl/g (measured in 0.6% strength solution in toluene at 25° C.).

I. PREPARATION OF THE POLYMERIC CARRIER ACCORDING TO THE INVENTION

EXAMPLE 1

(Copolymer of N-methylolacrylamide, N-vinylpyrrolidone and N,N'-methylenebisacrylamide)

800 ml of low viscosity liquid paraffin DAB 7 (dispersing agent), 2.0 g of a copolymer of maleic anhydride and 1-octadecene (molar ratio 1:1; RSV value 0.064 dl/g, measured in 0.6% strength solution in toluene at 25° C.), 33.3 g of N-methylolacrylamide, 36.7 g of N-vinylpyrrolidone, 30 g of N,N'-methylenebisacrylamide, 2 g of azodiisobutyronitrile, 212 ml of dimethylformamide and 90 ml of polyethylene glycol (molecular weight about 400) were initially introduced into a round-bottomed flask with a stirrer, thermometer, nitrogen-introduction tube and reflux condenser.

This mixture was then heated slowly with stirring. The exothermic polymerization reaction started at about 65° C., whereupon the temperature rose to about 80° C. This temperature was maintained by means of an oil bath with a thermostat for 1 hour, then the bath temperature was increased to 90° C. for four hours to complete polymerization. The heating bath was subsequently removed and the batch was allowed to cool to 40° C., with stirring. The stirring was then switched off, whereupon the polymer in the form of beads settled out after some time. The major amount of the liquid paraffin was then syphoned off and the residue was subsequently sucked off via a suction filter. The resulting polymer was then treated with petroleum ether, with stirring, in order to remove the adherent liquid paraffin. It was subsequently thoroughly stirred with methanol, then with acetone and finally was extracted with acetone at the boiling point in order to dissolve out the unreacted monomers and the dispersant. Finally, the polymer was dried in a vacuum oven at 50° C. overnight and was screened.

The yield of crosslinked copolymer was 95 g (=95% of theory).

Essentially the same product is obtained when a corresponding dispersing agent made from maleic anhydride and dodecene is employed.

15 g of the 50–100 μm screen fraction were swelled in 100 ml of epichlorohydrin for 16 hours, then heated at 115° C. for four hours and, after cooling to 25° C., filtered off with suction. The product was then stirred twice for 30 minutes with 200 ml of acetone each time, filtered off with suction and stored overnight in a vacuum drying oven at 40° C. under nitrogen.

Weighing showed 14.6 g of product in the form of beads having a bulk density of 340 g/l and an epoxide equivalent of 143.

EXAMPLE 2

(Copolymer of N-methylolacrylamide, N-vinylpyrrolidone and N,N'-methylenebisacrylamide)

900 ml of liquid paraffin (DAB 7), 0.2 g of the copolymer of maleic anhydride and vinyl stearyl ether described above, 44.1 g of N-methylolacrylamide, 48.4 g of N-vinylpyrrolidone, 7.5 g of N,N'-methylenebisacrylamide, 2 g of azodiisobutyronitrile, 126 ml of dimethylformamide and 48 ml of polyethylene glycol (molecular weight 400) were initially introduced into a cylindrical vessel having a cross-blade agitator, reflux condenser, thermometer and nitrogen-introduction tube. The bath temperature was slowly raised to 65° C., while passing in nitrogen, then polymerization and working up were carried out as described in Example 1.

The yield of crosslinked product was 89.1 g (=89.1% of theory).

An essentially identical product is obtained when a corresponding copolymer of maleic anhydride and vinyl dodecyl ether is employed as the dispersing agent.

The conversion into the product containing epoxide groups was carried out in the manner indicated in Example 1, paragraph 5. The product in the form of beads had a bulk density of 367 g/l and an epoxide equivalent of 320.

EXAMPLE 3

(Copolymer of N-methylolacrylamide, N-vinyl-N-methylacetamide and N,N'-methylenebisacrylamide)

The following system was subjected to polymerization in the apparatus described in Example 1 under the conditions indicated in this Example 1:

900 ml of liquid paraffin, 0.2 g of the copolymer of maleic anhydride and vinyl stearyl ether used in Example 2, 46.7 g of N-methylolacrylamide, 45.8 g of N-vinyl-N-methylacetamide, 7.5 g of N,N'-methylenebisacrylamide, 2.0 g of azodiisobutyronitrile, 126 ml of dimethylformamide and 48 ml of polyethylene glycol (molecular weight 400).

The working up was likewise as described in Example 1.

The yield of crosslinked copolymer was 94 g (=94% of theory).

The conversion into the product containing epoxide groups was carried out in the manner indicated in Example 1, paragraph 5. The product in the form of beads had a bulk density of 287 g/l and an epoxide equivalent of 193.

EXAMPLE 4

(Copolymer of N-methylolacrylamide, N-vinylpyrrolidone and N,N'-divinylethyleneurea)

The following system was subjected to polymerization under the conditions of Example 1 in the apparatus of Example 2:

900 ml of liquid paraffin, 0.2 g of the copolymer of maleic anhydride and vinyl stearyl ether used in Example 2, 40.5 g of N-methylolacrylamide, 44.5 g of N-vinylpyrrolidone, 15 g of N,N'-divinylethyleneurea, 2.0 g of azodiisobutyronitrile, 126 ml of dimethylformamide and 48 ml of polyethylene glycol (molecular weight 400).

The working up was as described in Example 1.

Yield: 96 g (=96% of theory) of crosslinked copolymer.

The conversion into the product containing epoxide groups was carried out in the manner indicated in Example 1, paragraph 5. The product in the form of beads had a bulk density of 493 g/l and an epoxide equivalent of 284.

EXAMPLE 5

(Copolymer of N-methylolacrylamide, N-vinylpyrrolidone and glyoxabisacrylamide)

The following system was subjected to polymerization under the conditions of Example 1 in the apparatus of Example 2:

900 ml of liquid paraffin, 0.2 g of copolymer of maleic anhydride and vinyl stearyl ether (as in Example 2), 44.1 g of N-methylolacrylamide, 48.4 g of N-vinylpyrrolidone, 7.5 g of glyoxabisacrylamide, 2.0 g of azodiisobutyronitrile, 126 g of dimethylformamide and 48 ml of polyethylene glycol (molecular weight 400).

The working up was carried out as in Example 1.

Yield: 94 g (=94% of theory) of crosslinked copolymer.

The conversion into the product containing epoxide groups was carried out in the manner indicated in Example 1, paragraph 5. The product had a bulk density of 340 g/l and an epoxide equivalent of 442.

EXAMPLE 6

(Copolymer of N-methylolacrylamide,
N-vinylpyrrolidone and
N,N',N''-trisacryloylperhydrotriazine)

The following system was subjected to polymerization under the conditions of Example 1 in the apparatus of Example 2:

900 ml of liquid paraffin, 0.2 g of copolymer of maleic anhydride and vinyl stearyl ether (as in Example 2), 45.3 g of N-methylolacrylamide, 49.7 g of N-vinylpyrrolidone, 5.0 g of N,N',N''-trisacryloylperhydrotriazine, 2 g of azodiisobutyronitrile, 126 ml of dimethylformamide and 48 ml of polyethylene glycol (molecular weight 400).

The working up was as described in Example 1.

Yield: 79 g (=79% of theory) of crosslinked copolymer.

The conversion into the product containing epoxide groups was carried out in the manner indicated in Example 1, paragraph 5. The product in the form of beads had a bulk density of 233 g/l and an epoxide equivalent of 357.

EXAMPLE 7

(Copolymer of N-methylolacrylamide,
N-vinylpyrrolidone and N,N'-methylenebisacrylamide)

The following system was subjected to polymerization under the conditions of Example 1 in the apparatus of Example 2:

900 ml of liquid paraffin, 0.2 g of copolymer of maleic anhydride and vinyl stearyl ether (as in Example 2), 40.5 g of N-methylolacrylamide, 44.5 g of N-vinylpyrrolidone, 15 g of N,N'-methylenebisacrylamide, 2 g of azodiisobutyronitrile, 126 g of dimethylformamide and 45 ml of ethylene glycol.

The working up was carried out as in Example 1.

Yield: 96 g (=96% of theory) of crosslinked copolymer.

The conversion into the product containing epoxide groups was carried out in the manner indicated in Example 1, paragraph 5. The product had a bulk density of 553 g/l and an epoxide equivalent of 211.

EXAMPLE 8

(Copolymer of N-methylolacrylamide,
N-vinylpyrrolidone and N,N'methylenebisacrylamide)

The following system was subjected to polymerization under the conditions of Example 1 in the apparatus of Example 2:

900 ml of liquid paraffin, 1 g of copolymer of maleic anhydride and 1-octadecene (as in Example 1), 40.5 g of N-methylolacrylamide, 44.5 g of N-vinylpyrrolidone, 15 g of methylenebisacrylamide, 2 g of azodiisobutyronitrile and 45 ml of glycerol triacetate.

The polymerization time was one hour at 70° C. and 4 hours at 80° C.

The working up was carried out as described in Example 1.

Yield: 98 g (=98% of theory) of crosslinked copolymer.

The conversion into the product containing epoxide groups was carried out in the manner indicated in Example 1, paragraph 5. The product in the form of beads had a bulk density of 240 g/l and an epoxide equivalent of 214.

EXAMPLE 9

(Copolymer of N-methylolacrylamide,
N-vinylpyrrolidone and N,N'-methylenebisacrylamide)

The following system was subjected to polymerization under the conditions of Example 1 in the apparatus of Example 2:

900 ml of liquid paraffin, 0.2 g of copolymer of maleic anhydride and vinyl stearyl ether (according to Example 2), 44.1 g of N-methylolacrylamide, 48.4 g of N-vinylpyrrolidone, 7.5 g of N,N'-methylenebisacrylamide, 2.0 g of ammonium peroxydisulfate, 30 ml of distilled water and 106 ml of diacetone alcohol.

The polymerization time was 5 hours at 80° C. The working up was carried out as in Example 1.

Yield: 72 g (=72% of theory).

The conversion into the product containing epoxide groups was carried out in the manner indicated in Example 1, paragraph 5. The product in the form of beads had a bulk density of 180 g/l and an epoxide equivalent of 460.

EXAMPLE 10

(Copolymer of N-(2-hydroxyethyl)acrylamide,
N-vinylpyrrolidone and N,N'-methylenebisacrylamide)

800 ml of low viscosity liquid paraffin DAB 7 (dispersing agent), 2.0 g of a copolymer of maleic anhydride and 1-octadecene (molar ratio 1:1, RSV value 0.064 dl/g measured in 0.6% strength solution in toluene at 25° C.), 43.3 g of N-(2-hydroxyethyl)acrylamide, 41.7 g of N-vinylpyrrolidone, 15 g of N,N'-methylenebisacrylamide, 2 g of azodiisobutyronitrile, 212 ml of dimethylformamide and 90 ml of polyethylene glycol (molecular weight about 400) were initially introduced into a round-bottomed flask with a stirrer, thermometer, nitrogen-introduction tube and reflux condenser.

This mixture was then slowly heated, with stirring. The exothermic polymerization reaction started at about 65° C., whereupon the temperature rose to about 80° C. This temperature was maintained by means of an oil bath with a thermostat for 1 hour, then the bath temperature was increased to 90° C. for four hours to complete polymerization. The heating bath was subsequently removed and the batch was allowed to cool to 40° C., with stirring. The stirring was then switched off, whereupon the polymer in the form of beads settled out after some time. The major amount of the liquid paraffin was then syphoned off and the residue was subsequently sucked off via a suction filter. The resulting polymer was then treated with petroleum ether to remove the adherent liquid paraffin. It was subsequently thoroughly stirred with methanol, then with acetone and finally extracted with acetone at the boiling point in order to dissolve out the unreacted monomers and the dispersant. Finally, the polymer was dried in a vacuum oven at 50° C. overnight, and was screened.

The yield of crosslinked copolymer was >95 g (=>95% of theory).

Essentially the same product is obtained when a corresponding dispersion stabilizer made from maleic anhydride and dodecene is employed.

15 g of the 50 to 100 μm screen fraction were swelled in 100 ml of epichlorohydrin for 16 hours, then heated at 115° C. for four hours and, after cooling to 25° C., filtered off with suction. It was then stirred twice for 30 minutes with 200 ml of acetone each time, filtered off with suction and stored overnight in a vacuum drying oven at 40° C. under nitrogen.

Weighing showed 14.3 g of product in the form of beads having a bulk density of 440 g/l and an epoxide equivalent of 182.

EXAMPLE 11

(Copolymer of N-(2-hydroxyethyl)acrylamide, N-vinylpyrrolidone and N,N'-ethylenebisacrylamide)

900 ml of liquid paraffin (DAB 7), 0.2 g of the copolymer made of maleic anhydride and vinyl stearyl ether described in Example 1, 47.1 g of N-(2-hydroxyethyl)-acrylamide, 45.4 g of N-vinylpyrrolidone, 7.5 g of N,N'-ethylenebisacrylamide, 2 g of azodiisobutyronitrile, 126 ml of dimethylformamide and 48 ml of polyethylene glycol (molecular weight 400) were initially introduced into a cylindrical vessel having a cross-blade agitator, reflux condenser, thermometer and nitrogen-introduction tube. The bath temperature was slowly raised to 65° C., while passing in nitrogen, then polymerization and working up were carried out as described in Example 1.

The yield of crosslinked product was 92.3 g (=92.3% of theory).

The conversion into the product containing epoxide groups was carried out in the manner indicated in Example 1, paragraph 5. The product in the form of beads had a bulk density of 385 g/l and an epoxide equivalent of 340.

EXAMPLE 12

(Copolymer of N-(2-hydroxyethyl)acrylamide, N-vinylpyrrolidone and N,N'-hexamethylenebisacrylamide)

900 ml of liquid paraffin (DAB 7), 0.2 g of the copolymer of maleic anhydride and vinyl stearyl ether described in Example 1, 43.3 g of N-(2-hydroxyethyl)acrylamide, 41.7 g of N-vinylpyrrolidone, 15 g of hexamethylenebisacrylamide, 2 g of azodiisobutyronitrile, 126 ml of dimethylformamide and 48 ml of polyethylene glycol (molecular weight 400) were initially introduced into a cylindrical vessel having a cross-blade agitator, reflux condenser, thermometer and nitrogen-introduction tube. The temperature of the bath was slowly raised to 65° C., while passing in nitrogen, then polymerization and working up were carried out as described in Example 1.

The yield of crosslinked product was 85.3 g (=85.3% of theory).

The conversion into the product containing epoxide groups was carried out in the manner indicated in Example 1, paragraph 5. The product in the form of beads had a bulk density of 420 g/l and an epoxide equivalent of 280.

EXAMPLE 13

(Copolymer of N-(2-hydroxyethyl)acrylamide, N-vinylpyrrolidone and N,N'-divinylethyleneurea)

900 ml of liquid paraffin (DAB 7), 0.2 g of the copolymer of maleic anhydride and vinyl stearyl ether described in Example 1, 43.3 g of N-(2-hydroxyethyl)-acrylamide, 41.7 g of N-vinylpyrrolidone, 15.0 g of N,N'-divinylethyleneurea, 2 g of azodiisobutyronitrile, 126 ml of dimethylformamide and 48 ml of polyethylene glycol (molecular weight 400) were initially introduced into a cylindrical vessel having a cross-blade agitator, reflux condenser, thermometer and nitrogen-introduction tube. The bath temperature was slowly raised to 65° C., while passing in nitrogen, then polymerization and working up were carried out as described in Example 1.

The yield of crosslinked product was 87.3 g (=87.3% of theory).

The conversion into the product containing epoxide groups was carried out in the manner indicated in Example 1, paragraph 5. The product in the form of beads had a bulk density of 395 g/l and an epoxide equivalent of 287.

II. REACTION OF THE POLYMERIC CARRIER ACCORDING TO THE INVENTION WITH BIOLOGICALLY ACTIVE SUBSTANCES

EXAMPLE 14

1,100 µl of a penicillin acylase solution (25 mg ml, 243 U/ml), which was 1 molar in potassium phosphate (buffer) and had a pH of 8.0, were added to 0.2 g of a carrier prepared according to Example 1. After binding for 72 hours, the beads were thoroughly washed with 1 molar saline and with buffer solution. The yield of material moist from the filter funnel was 678 mg, with 270 units/g measured in an autotitrator at 37° C. and a pH of 7.8 using potassium penicillinate as the substrate.

This was 916 units/g based on dry weight. After balancing the initial activity and the activity in the wash water, the yield of binding (=the activity on the carrier: activity made available) which remained was 69%. The $\eta$ value was 0.82. ($\eta$=activity found/activity made available less activity in the wash water).

EXAMPLE 15

1,000 µl of a trypsin solution (6.25 mg/ml, 345 U/ml), which was $1.6 \times 10^{-2}$ molar in benzamidine and 1 molar in potassium phospate (buffer) and had a pH of 7.8, were added to 0.2 g of a carrier prepared according to Example 2. After binding for 72 hours, the beads were thoroughly washed with 1 molar saline and with buffer solution. The yield of material moist from the filter funnel was 589 mg, with 485 units/g measured in an autotitrator at 37° C. and a pH of 8.1 using N'-benzoyl-L-arginine ethyl ester hydrochloride (BAEE) as the substrate. This was 1,429 units/g based on dry weight. After balancing the initial activity and the activity in the wash water, the yield of binding which remained was 60%. The $\eta$ value was 0.61.

EXAMPLE 16

1,000 µl of a urease solution (30 mg/ml, 45.5 U/ml), which was 1 molar in potassium phosphate (buffer) and had a pH of 8.0, were added to 0.2 g of a carrier prepared according to Example 2. After binding for 72 hours, the beads were thoroughly washed with 1 molar saline and with buffer solution. The yield of material moist from the filter funnel was 561 mg, with 47 units/g measured in an autotitrator at 30° C. and a pH of 6.1 using urea as the substrate. This was 132 units/g based on dry weight. After balancing the initial activity and the activity in the wash water, the yield of binding which remained was 83%. The $\eta$ value was 0.87.

EXAMPLE 17

1,000 µl of a penicillin acylase solution (25 mg ml, 243 U/ml), which was 1 molar in potassium phosphate (buffer) and had a pH of 8.0, were added to 0.2 g of a carrier prepared according to Example 2. After binding for 72 hours, the beads were thoroughly washed with 1 molar saline and with buffer solution. The yield of material moist from the filter funnel was 597 mg, with 356 units/g measured in an autotitrator at 37° C. and a pH of 7.8 using potassium penicillinate as the substrate. This was 1,063 units/g based on dry weight. The yield of binding was 88%. The $\eta$ value was 0.90.

EXAMPLE 18

900 μl of a penicillin acylase solution (25 mg ml, 280 U/ml), which was 1 molar in potassium phosphate (buffer) and had a pH of 80.0, were added to 0.2 g of a carrier prepared according to Example 11. After binding for 72 hours, the beads were thoroughly washed with 1 molar saline and with buffer solution. The yield of material moist from the filter funnel was 665 mg, with 250 units/g measured in an autotitrator at 37° C. and a pH of 7.8 using potassium penicillinate as the substrate. This was 831 units/g based on dry weight. After balancing the initial activity and the activity in the wash water, the yield of binding (=activity on the carrier: activity made available) which remained was 67%. The $\eta$ value was 0.68.

EXAMPLE 19

700 μl of a trypsin solution (6.25 mg/ml, 440 U/ml) which was $1.6 \times 10^{-2}$ molar in benzamidine and 1 molar in potassium phosphate (buffer) and had a pH of 7.8, was added to 0.2 g of a carrier prepared according to Example 12. After binding for 72 hours, the beads were thoroughly washed with 1 molar saline and with buffer solution. The yield of material moist from the filter funnel was 657 mg, with 460 units/g measured in an autotitrator at 37° C. and a pH of 8.1 using N'-benzoyl-L-arginine ethyl ester hydrochloride (BAEE) as the substrate. This was 1,200 units/g based on dry weight. After balancing the initial activity and the activity in the wash water, the yield of binding which remained was 80%. The $\eta$ value was 0.9.

EXAMPLE 20

1,000 μl of a penicillin acylase solution (25 mg ml, 293 U/ml), which was 1 molar in potassium phosphate (buffer) and had a pH of 8.0, were added to 0.2 g of a carrier prepared according to Example 13. After binding for 72 hours, the beads were thoroughly washed with 1 molar saline and with buffer solution. The yield of material moist from the filter funnel was 661 mg, with 310 units/g measured in an autotitrator at 37° C. and a pH of 7.8 using potassium penicillinate as the substrate. This was 1,025 units/g based on dry weight. The yield of binding was 70%. The $\eta$ value was 0.95.

We claim:

1. A polymer essentially composed of units derived from monomers of the formula

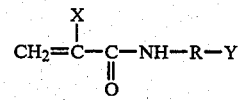
(I)

in which X is hydrogen or methyl, R denotes an aliphatic hydrocarbon radical having 1 to 12 carbon atoms, and Y represents OH or NH$_2$, and of units which are derived from at least one other monomer which can be copolymerized with monomers of the formula (I), the mean particle size of the polymer particles being in the range from 20 to 800 μm, which comprises the polymer particles having an essentially spherical shape and a mean pore diameter of 5 to 2,000 nm.

2. The polymer as claimed in claim 1, which has a mean pore diameter of 10 to 1,000 nm.

3. The polymer as claimed in claim 1, wherein R in the formula (I) is an aliphatic hydrocarbon radical having 1 to 6 carbon atoms, and Y is a terminal (primary) OH group.

4. The polymer as claimed in claim 3, wherein R is methylene.

5. The polymer as claimed in claim 1, which is crosslinked by reason of the incorporation of crosslinked monomer units.

6. The polymer as claimed in claim 5 which also contains units derived from monomers having hydrophilic groups.

7. The polymer as claimed in claim 1, wherein at least some of the radicals Y have been reacted with a spacer.

8. The polymer as claimed in claim 7, wherein the spacer introduces epoxide units in an amount of 0.1 to 20 mole-% relative to the total polymer.

9. The polymer as claimed in claim 1, which is essentially composed of 10 to 80 mole-% of units which derive from monomers of the formula (I), of 20 to 50 mole-% of units which derive from monomers having hydrophilic groups, and of 1 to 50 mole-% of units which derive from monomers having crosslinking groups.

10. A process for the preparation of a polymer as claimed in claim 1, by polymerization of compounds of the formula

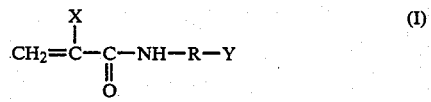
(I)

in which X, R and Y have the abovementioned meaning, with at least one other monomer which can be copolymerized with it, the polymerization being carried out in a liquid dispersing agent which, under the polymerization conditions, does not dissolve the monomers and the polymer, in the presence of a radical initiator and a dispersion stabilizer, which comprises using, as the dispersion stabilizer, a copolymer of maleic anhydride and a vinyl alkyl ether having 6 to 30 carbon atoms in the alkyl group, or a vinyl ester having 6 to 30 carbon atoms in the carboxylic acid group, or a relatively long-chain α-olefin having 8 to 30 carbon atoms.

11. The process as claimed in claim 10, wherein the dispersion stabilizer is used in amounts of 0.005 to 10% by weight based on the mixture of monomers.

12. The process as claimed in claim 10, wherein the dispersion stabilizer is an alternating copolymer.

13. The process as claimed in claim 10, wherein the RSV value of the copolymer employed as the dispersion stabilizer is between 0.01 and 1.0 dl/g (measured in 0.6% strength solution in toluene at 25° C.).

14. The process as claimed in claim 10, wherein the vinyl alkyl ether is vinyl stearyl ether, and the relatively long-chain α-olefin is 1-ocatadecene.

15. The process as claimed in claim 10, wherein hydrocarbons having 6 to 20 carbon atoms or low viscosity liquid paraffin are employed as the liquid dispersing agent.

16. The process as claimed in claim 10, wherein, to increase the porosity of the bead polymer, the polymerization system contains substances which are readily soluble in the monomers or are miscible with them and are virtually insoluble in the dispersing agent.

* * * * *